(12) United States Patent
Major et al.

(10) Patent No.: US 9,211,518 B2
(45) Date of Patent: Dec. 15, 2015

(54) PROCESS AND APPARATUS FOR PRODUCTION AND FILTRATION OF AMINOALCOHOLS USING A CONTINUOUS STIRRED TANK SLURRY REACTOR

(75) Inventors: Michael D. Major, Evanston, IL (US); John D. Gummere, Monroe, LA (US)

(73) Assignee: ANGUS CHEMICAL COMPANY, Buffalo Grove, IL (US)

( * ) Notice: Subject to any disclaimer, the term of this patent is extended or adjusted under 35 U.S.C. 154(b) by 0 days.

(21) Appl. No.: 14/128,398

(22) PCT Filed: Jun. 8, 2012

(86) PCT No.: PCT/US2012/041482
§ 371 (c)(1),
(2), (4) Date: Dec. 20, 2013

(87) PCT Pub. No.: WO2012/177419
PCT Pub. Date: Dec. 27, 2012

(65) Prior Publication Data
US 2014/0121413 A1    May 1, 2014

Related U.S. Application Data

(60) Provisional application No. 61/500,730, filed on Jun. 24, 2011.

(51) Int. Cl.
| | |
|---|---|
| *B01J 8/22* | (2006.01) |
| *C07C 213/02* | (2006.01) |
| *C07C 209/52* | (2006.01) |
| *B01J 8/00* | (2006.01) |

(Continued)

(52) U.S. Cl.
CPC ....... *B01J 8/228* (2013.01); *B01J 8/006* (2013.01); *B01J 8/1809* (2013.01); *B01J 8/222* (2013.01); *C07C 29/151* (2013.01); *C07C 29/68* (2013.01); *C07C 209/52* (2013.01); *C07C 213/02* (2013.01); *C07C 2101/16* (2013.01)

(58) Field of Classification Search
CPC .................. B01J 8/222; B01J 8/228
USPC .................. 422/212, 616, 140, 147
See application file for complete search history.

(56) References Cited

U.S. PATENT DOCUMENTS 3,546,296 A * 12/1970 Gobron et al. ............. 564/422
5,599,849 A    2/1997 Jager et al.

(Continued)

FOREIGN PATENT DOCUMENTS

| | | |
|---|---|---|
| CN | 1739846 | 3/2006 |
| CN | 1822896 | 8/2006 |

(Continued)

OTHER PUBLICATIONS

International Application No. PCT/US2012041482, Notification of Transmittal of the International Search Report and the Written Opinion of the International Searching Authority, Nov. 9, 2012.

(Continued)

*Primary Examiner* — Lessanework Seifu
(74) *Attorney, Agent, or Firm* — Foley & Lardner LLP

(57) ABSTRACT

Disclosed are processes and apparatuses for producing a reaction product and enabling the reaction product to be removed from a reactor operating at an elevated pressure, while simultaneously maintaining the gas pressure and retaining the catalyst inside the apparatus.

20 Claims, 2 Drawing Sheets

(51) Int. Cl.
　　*B01J 8/18*　　(2006.01)
　　*C07C 29/68*　　(2006.01)
　　*C07C 29/151*　　(2006.01)

(56) References Cited

U.S. PATENT DOCUMENTS

| | | | |
|---|---|---|---|
| 5,900,159 A * | 5/1999 | Engel et al. | 210/788 |
| 7,488,760 B2 * | 2/2009 | Vogel | 518/700 |
| 2001/0027257 A1 | 10/2001 | Marion | |
| 2002/0035163 A1 | 3/2002 | Vogel et al. | |
| 2002/0128330 A1 | 9/2002 | Anderson | |
| 2007/0197667 A1 | 8/2007 | Vogel | |
| 2010/0216896 A1 | 8/2010 | Wang et al. | |
| 2012/0071316 A1 | 3/2012 | Voss et al. | |

FOREIGN PATENT DOCUMENTS

| | | |
|---|---|---|
| CN | 101209403 | 7/2008 |
| DE | 3245318 | 6/1984 |
| GB | 1264518 | 2/1972 |
| JP | 2008-001909 | 1/2008 |
| JP | 2009-509765 | 3/2009 |
| WO | WO-2005/005038 | 1/2005 |
| WO | WO-2007/041726 | 4/2007 |
| WO | WO-2010/125025 | 11/2010 |
| WO | WO2010125025 | 11/2010 |
| WO | WO2010139728 | 12/2010 |

OTHER PUBLICATIONS

Office Action issued on Japanese Application 2014-517008, mailed Feb. 3, 2015 (English translation provided).
Office Action on Chinese Application 201280031102.9, mailed Apr. 10, 2015, English translation provided.
W.L. McCabe and J.C. Smith, "Unit Operations of Chemical Engineering," 3rd Ed.(1976), p. 17 (3 pages).
English Translation of the Notice of Preliminary Rejection issued on Korean Application 2014-7001828, mailed Jun. 17, 2015.

* cited by examiner

PROCESS AND APPARATUS FOR PRODUCTION AND FILTRATION OF AMINOALCOHOLS USING A CONTINUOUS STIRRED TANK SLURRY REACTOR

CROSS REFERENCE TO RELATED APPLICATION

This application is a U.S. national phase of International Application No. PCT/US2012/041482, filed Jun. 8, 2012, which claims priority to U.S. Provisional Application No. 61/500,730, filed Jun. 24, 2011; the disclosures of both of these applications are incorporated herein by reference in their entireties.

FIELD

This invention relates to processes and apparatuses for manufacturing chemicals at high pressure using catalysts and reactive gases. More particularly, this invention relates to processes and apparatuses for separating the reaction product from the catalyst and the high pressure gas.

BACKGROUND

Valuable chemicals, such as aminoalcohols, are often produced in equipment that operates at high temperature and pressure utilizing catalysts and reactive gasses, such as hydrogen. A critical part of the manufacturing process involves separating the valuable product from the catalyst and the high pressure gas. It is common practice to vent the reactors to relieve the pressure and to filter the catalyst to separate it from the product. Due to the hazards frequently associated with handling the gas and/or the catalyst it is desirable to minimize this handling. Additionally, it is desirable to avoid venting the gas due to the lost material and time that this step incurs. It is also desirable to minimize filtration of the catalyst since this also may be time consuming and costly and somewhat hazardous.

Catalytic hydrogenations over heterogeneous catalysts may be carried out using fixed bed reactors in order to obtain the advantages of a continuous process. For various reactions, fixed bed reactors are, however, unsuitable, since, to achieve complete conversion in a single pass, such reactors would to have to be very large. Additionally, the amount of heat that comes from the hydrogenation of certain compounds can cause problems with regard to heat removal, such as loss of selectivity in the reactor. To reduce the amount of heat, partial conversion and recycle may be used; however, partial conversion may not be appropriate because the selectivity and yield of reaction are adversely affected. Other processes use a bubble column reactor; however, a second (finishing) reactor is often used to provide more complete conversion.

Desirable catalysts for the production of aminoalcohols include unsupported base-metal catalysts such as nickel or cobalt, often in their sponge form. The properties of these catalysts makes filtration significantly more difficult in comparison to supported metal catalysts. A need exists, therefore, for a system that enables the valuable product to be removed continuously from a hydrogenation reactor operating at elevated pressure while simultaneously maintaining the gas pressure and retaining the valuable catalyst inside of the reactor system.

BRIEF SUMMARY

In one aspect, an illustrative embodiment provides an apparatus comprising a reactor for reacting a first reactant with a second reactant over a catalyst to produce a reaction product; a filtration apparatus for filtering the catalyst from the reaction product, such that the catalyst accumulates in the filtration apparatus; and a backpulse system for returning accumulated catalyst from the filtration apparatus to the reactor.

In another aspect, an illustrative embodiment provides a process comprising reacting a first reactant with a second reactant over a catalyst in a reactor to produce a reaction product; filtering the reaction product and the catalyst through a filtration apparatus, such that the catalyst accumulates in the filtration apparatus. The process further comprises returning accumulated catalyst from the filtration apparatus to the reactor using at least one backwards pulse from a backpulse system.

In another aspect, an illustrative embodiment provides a process comprising reacting a nitroalcohol with hydrogen over an activated sponge metal catalyst in a reactor to produce an aminoalcohol, wherein the reactor is a stirred tank slurry reactor; and filtering the aminoalcohol and the catalyst through a filtration apparatus, such that the catalyst accumulates in the filtration apparatus. The process further comprises returning accumulated catalyst from the filtration apparatus to the reactor using at least one backwards pulse from a backpulse system, wherein the backpulse system comprises at least a first vessel and a second vessel, and wherein a backpulse gas from the second vessel increases the pressure in the first vessel, such that the pressure in the first vessel is greater than the reactor pressure.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In one aspect, an apparatus for producing a reaction product is provided. The apparatus beneficially enables the reaction product to be removed from a reactor operating at an elevated pressure, while simultaneously maintaining the gas pressure and retaining the catalyst inside the apparatus.

Figure 1:
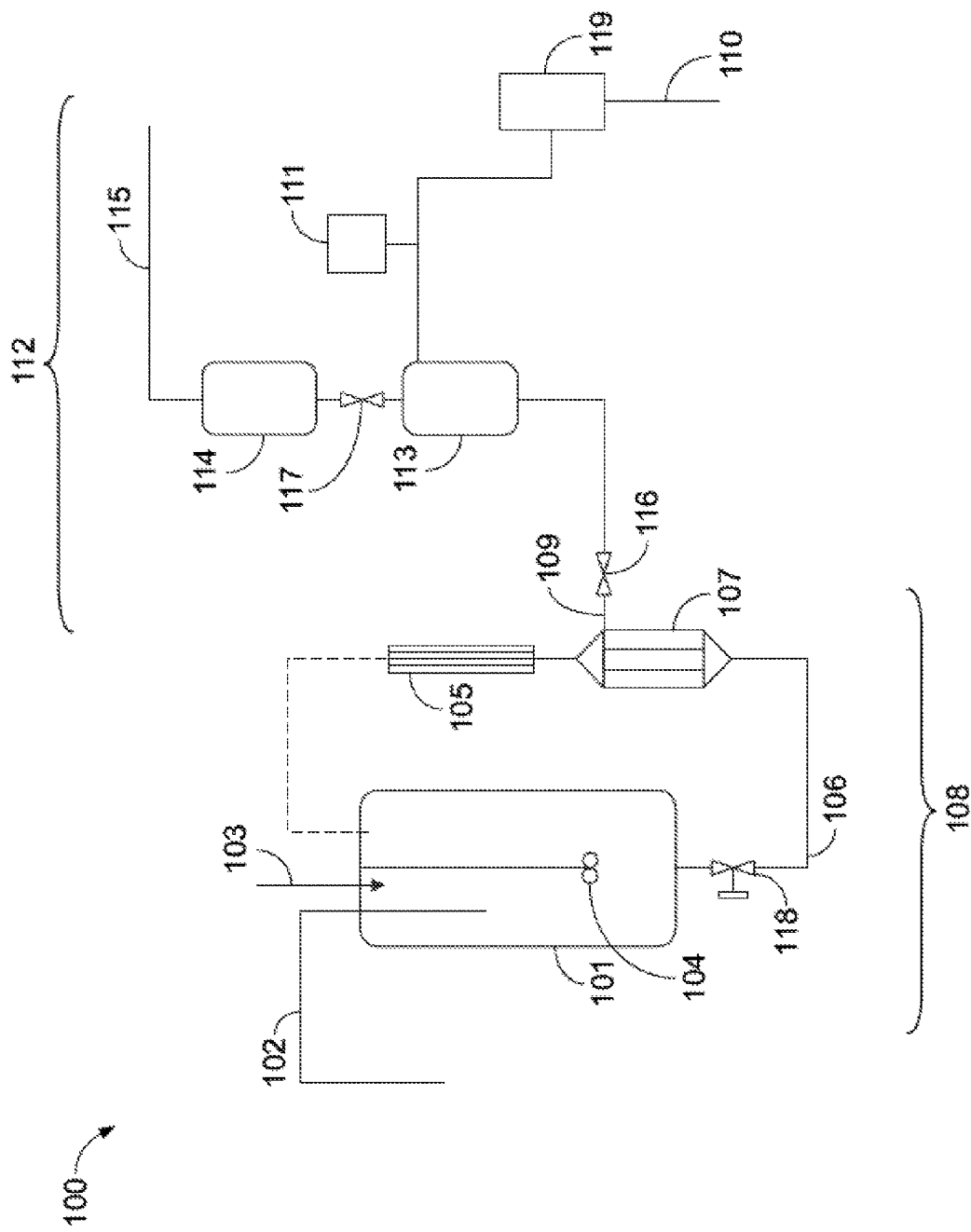
FIG. 1 is a schematic diagram of an apparatus.

FIG. 1 illustrates an apparatus 100 for continuously removing a reaction product from a reactor while retaining a catalyst inside the apparatus 100. At least a first reactant and a second reactant may be introduced into a reactor 101 through a reactant feedstock 102. The first reactant may be, for example, nitrobenzene, nitrotoluene, 2-nitro-2-methyl-1-propanol, glucose, a benzyl ether, an imine, or Resorcinol. Other reactants may also be used. The second reactant may be a reactive gas, such as hydrogen. In an illustrative embodiment, the hydrogen gas is added separately in an optional reactant/solvent feedstock 103. The reactor 101 may be built according to various designs, depending on the desired reaction outcome. For example, the reactor 101 may be a stirred, slurry type reactor, which provides for excellent heat transfer and provides good control of temperature and conversion. The reactor 101 may be fitted with internal coils and an external jacket for cooling. The reactor 101 may also be fitted with an agitator 104 to ensure adequate mixing and heat transfer within the reactor in order to achieve the desired reaction results. In alternative embodiments, it may be desirable to add heat to the reactor, either through the internal coils, the jacket, or both. The apparatus 100 may also include an external heat exchanger 105.

A catalyst and a solvent may be introduced into the reactor 101. The catalyst may be introduced into the reactor 101 separate from the solvent or with the solvent. Depending on the reaction chemistry, the reactants, a product, and/or a solvent may be introduced to the reactor 101. In a preferred embodiment, the solvent and the final product may be introduced into the reactor. In alternative embodiments, the solvent may be introduced through the reactant feedstock 102. In other embodiments, it may be advantageous to add the solvent separately, such as through the reactant/solvent feedstock 103. One advantage of adding the solvent separately would be that the solvent would not have to be blended with the feed prior to entry into the reactor 101. The solvent may be, for example, methanol, isopropanol, or other commonly used solvents.

The catalyst may be a solid unsupported base-metal catalyst, such as nickel or cobalt, which may be in its sponge form. In alternative embodiments, the catalyst may be a supported catalyst such as palladium, platinum, gold ruthenium, rhodium, or iridium on supports such as carbon, silica, alumina, clay, zeolites, or other supports or catalysts commonly used.

The first reactant and the second reactant may react at a reactor pressure and a reactor temperature, such that a reaction product is formed. The reactor pressure may be between about $3.45 \times 10^5$ Pa (50 psig) and about $6.98 \times 10^6$ Pa (1000 psig), more preferably between about $2.07 \times 10^6$ Pa (300 psig) and about $6.98 \times 10^6$ Pa (1000 psig), and most preferably between about $4.14 \times 10^6$ Pa (600 psig) and about $5.52 \times 10^6$ Pa (800 psig). The reactor temperature may be between about 26.7 degrees Celsius (80 degrees Fahrenheit) and about 148.9 degrees Celsius (300 degrees Fahrenheit), more preferably between about 37.8 degrees Celsius (100 degrees Fahrenheit) and about 82.2 degrees Celsius (180 degrees Fahrenheit), and most preferably between about 48.9 degrees Celsius (120 degrees Fahrenheit) and about 76.7 degrees Celsius (170 degrees Fahrenheit).

The reactor contents 106, including the reaction product, the catalyst, and the solvent, may be introduced into a filtration apparatus 107. In alternative embodiments in which the reaction does not proceed to completion, the first reactant and the second reactant may also be introduced into the filtration apparatus 107. The reactor 101 and filtration apparatus 107 may comprise a reaction system 108. The reaction system 108 may also include the external heat exchanger 105. The design of the filtration apparatus allows for continuous circulation of the reactor contents and continuous removal of the reaction product while keeping the catalyst inside the reaction system 108. The filtration apparatus may include filter elements, such as porous ceramic filter elements or sintered metal elements. Other materials may also be used to construct the filter elements. The catalyst may be retained inside the reaction system 108 while the reaction product and solvent are removed from the reaction system 108 through the filter elements. The filtered reaction product 109 and solvent may exit the apparatus 100 through outlet 110. Retention of the catalyst may be accomplished by maintaining a high flow rate in an axial direction through the filtration apparatus and allowing very slow filtration in a direction transverse to the main flow of the circulating mixture through the filter elements. Thus, the flow rate through the filter elements (the flow transverse to the main flow) is preferably controlled in order to avoid plugging the pores with fine particles of catalyst. In order to provide such control of the flow rate, a control apparatus 111 may be provided to control the flow rate and thus the pressure drop across the filtration apparatus. Too high of a pressure differential may allow the catalyst to become embedded in the filter elements, thus rendering it inoperable. However, as some minimum flow rate should preferably be maintained in order to provide for continuous operation, some pressure differential may exist.

As the operation of the filtration apparatus 107 continues for extended periods of time, very small quantities of the catalyst may accumulate on the filtration apparatus surface and possibly within the body of the filter elements. In order to prevent degradation of the performance of the filtration apparatus, a backpulse system 112 is provided. The backpulse system comprises a first vessel 113, attached to the outlet of the filtration apparatus 107, a second vessel 114, and a backpulse gas supply line 115. The backpulse system 112 operates by accumulating a small volume of catalyst-free liquid in the first vessel 113. The catalyst-free liquid may be the reactor product or a solvent.

The pressure in the first vessel 113 is maintained at a pressure above the reactor pressure by a backpulse gas in the second vessel 114. The backpulse gas may be supplied through the backpulse gas supply line 115. The backpulse gas may be, for example, hydrogen. At a designated time, valves 116, 117, and 118 may be opened to allow the liquid in the first vessel 113 to be pushed back through the filtration apparatus 107 into the reactor 101 by the backpulse gas in the second vessel 114. The designated time may be periodic, for example, every five minutes, or may be determined by pressure differential across the filter.

Preferably, the backwards pulse occurs infrequently, such as every twenty minutes. This backwards pulse effectively clears accumulated catalyst from the filter elements and returns it to the reactor. The duration of the backwards pulse may be between about 0.1 seconds and about 10 seconds, more preferably between about 0.2 seconds and about 2 seconds, and most preferably between about 0.5 seconds and about 1 second. The higher the pressure differential across the filter, the shorter in duration the backwards pulse may be. In alternative embodiments, the backwards pulse may be provided by a hydraulic piston or a pump. In such embodiments, the first vessel 113, the second vessel 114, and the backpulse gas supply line 115 are not use. The pressure differential across the filtration apparatus may be up to about $3.45 \times 10^5$ Pa (50 psig) above the rector pressure. For example, when the reactor pressure is at about $5.17 \times 10^6$ Pa (750 psig), the backpulse system pressure may be at about $5.52 \times 10^6$ Pa (800 psig). Lower or higher reactor pressures, and thus lower or higher backpulse system pressures, may also be used.

The rates of addition and removal of the first and second reactants and the reaction product is determined by the volume of reactor 101 and the kinetics of the chemical reaction. In order to maintain the correct average residence time in the reactor 101 and ensure that the extent of reaction is maintained at the desired level, the rates of addition. and removal are preferably equivalent. In an illustrative embodiment, complete conversion of the reactants is achieved. As a result, the average residence time can be much greater than the speed of reaction. For example, complete conversion may be desirable in reactions to produce aminoalcohols. In alternative embodiments, incomplete conversion may be desirable, for example, in fatty acid hydrogenation reactions.

The apparatus 100 may also comprise a third vessel 119. The reaction product may be introduced into the third vessel 119 prior to exiting through the outlet 110. The third vessel 119 may be used to vent any dissolved gases, such as hydrogen, that may still be in the reaction product. The third vessel 119 may also be used to maintain a liquid seal in order to prevent air from entering the apparatus.

EXAMPLES

The process for enabling the reaction product to be removed from a reactor operating at an elevated pressure, while simultaneously maintaining the gas pressure and retaining the catalyst inside the apparatus, is demonstrated experimentally.

Hydrogen is used to reduce 2-nitro-2-methyl-1-propanol (NMP) to 2-amino-2-methyl-1-propanol over Raney® nickel sponge catalyst. The differential pressure across the filtration apparatus is maintained at about $2.07 \times 10^4$ Pa (3 psi). Backpulse cycles range from about 5 minutes to about 20 minutes and the duration of the backwards pulse is between about 0.2 seconds and about 2 seconds. The reactor pressure is about $5.17 \times 10^6$ Pa (750 psig) and the reactor temperature is about 65 degrees Celsius (149 degrees Fahrenheit). Other aspects of the reaction for three different conditions are shown in Table 1 below.

TABLE 1

| | | Reaction Conditions | | |
| --- | --- | --- | --- | --- |
| | | Condition 1 | Condition 2 | Condition 3 |
| Feed Rate | kg/hr (lb/hr) | 72.6 (160) | 81.6 (180) | 90.7 (200) |
| Reactor Volume | kg (gal) | 28.4 (62.6) | 28.4 (62.6) | 28.4 (62.6) |
| Concentration NMP in Feed | mass fraction | 0.73 | 0.73 | 0.73 |
| NMP Concentration Feed Rate | kg/hr (lb/hr) | 53.0 (116.8) | 59.6 (131.4) | 66.2 (146) |
| Catalyst Loading | kg (lb) | 9.1 (20) | 9.1 (20) | 9.1 (20) |
| Feed Volume per Day | kg/day (lb/day) | 1741.8 (3840) | 1949.5 (4320) | 2177.2 (4800) |

Figure 2:
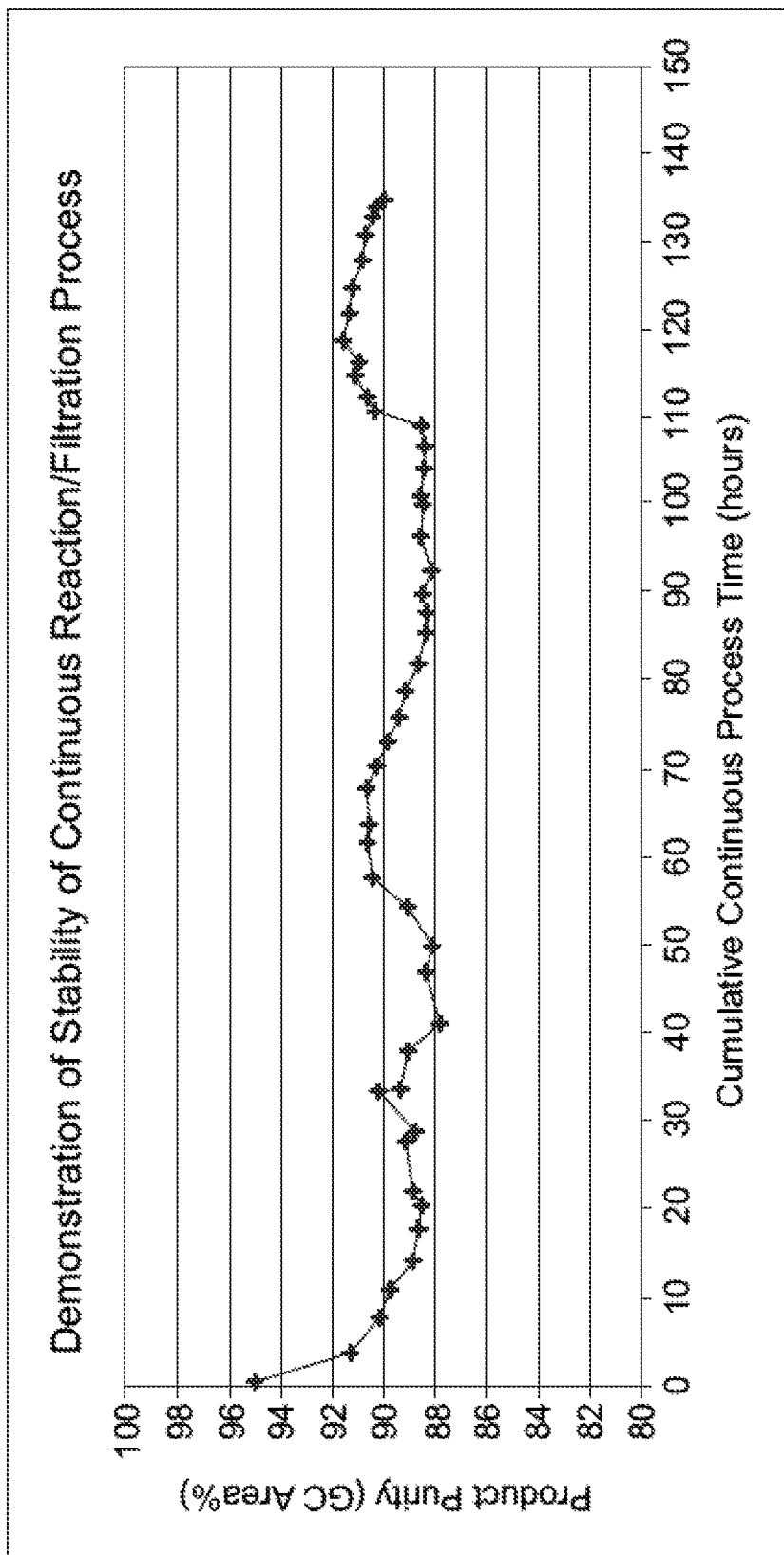
FIG. 2 is a graph of the reaction product purity during a continuous hydrogenation/filtration process.

As shown in FIG. 2, the reaction product purity remains fairly constant during hydrogenation and filtration over an extended period of time. Thus, the catalyst can be continuously filtered out of the reaction product stream during the hydrogenation.

This process may be used for other reactions in addition to the production of aminoalcohols. Such examples include:

Reduction of glucose to make sorbitol (over Raney-type nickel or cobalt catalysts).

Debenzylation of benzyl ethers using palladium on carbon catalyst (lower pressures are also useful here).

Hydrogenation of an imine using Raney® nickel catalyst (reactor temperature of about 50 degrees Celsius).

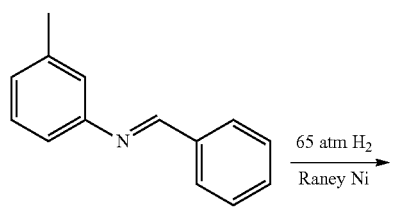
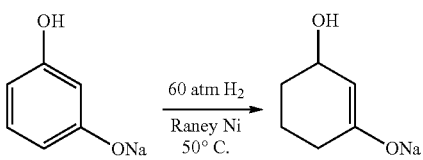
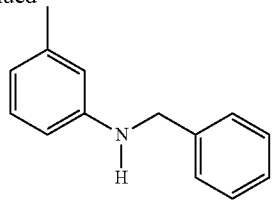

-continued

Partial hydrogenation of Resorcinol using Raney® nickel catalyst (reactor temperature of about 50 degrees Celsius).

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. An apparatus comprising:
    a reactor adapted to react a nitroalcohol with hydrogen over a catalyst at a reaction pressure between about $2 \times 10^6$ Pa and about $7 \times 10^6$ Pa to produce a reaction product, wherein the reaction product is an aminoalcohol;
    a filtration apparatus for filtering the catalyst from the reaction product, such that the catalyst accumulates in the filtration apparatus, wherein the filtration apparatus is located outside of the reactor; and
    a backpulse system for returning accumulated catalyst from the filtration apparatus to the reactor, wherein the backpulse system is provided by a hydraulic piston or a pump and is configured to push a liquid through the filtration apparatus to return the catalyst accumulated in the filtration apparatus to the reactor.

2. An apparatus according to claim 1, wherein the nitroalcohol and the hydrogen are introduced into the filtration apparatus.

3. An apparatus according to claim 1, wherein the backpulse system comprises a first vessel and a second vessel.

4. An apparatus according to claim 3, wherein the first vessel is attached to an outlet of the filtration apparatus.

5. An apparatus according to claim 3, wherein the pressure in the first vessel is greater than the pressure in the reactor.

6. An apparatus according to claim 1, wherein the reactor is a stirred tank slurry reactor.

7. An apparatus according to claim 1, wherein the reactor comprises a plurality of coils to facilitate heat transfer and an agitator to facilitate mass and heat transfer.

8. An apparatus according to claim 1, further comprising a heat exchanger.

9. An apparatus according to claim 4, wherein the pressure in the first vessel is greater than the pressure in the reactor.

10. An apparatus according to claim 5, wherein the reactor is a stirred tank slurry reactor.

11. A process comprising:
    reacting a first reactant with a second reactant over a catalyst in a reactor at a reaction pressure between about $2\times10^6$ Pa and about $7\times10^6$ Pa to produce a reaction product, wherein the reaction product is an aminoalcohol;
    filtering the reaction product and the catalyst through a filtration apparatus, such that the catalyst accumulates in the filtration apparatus, wherein the filtration apparatus is located outside of the reactor; and
    returning accumulated catalyst from the filtration apparatus to the reactor using at least one backwards pulse from a backpulse system, wherein the backpulse system is provided by a hydraulic piston or a pump and pushes a liquid through the filtration apparatus to return the catalyst accumulated in the filtration apparatus to the reactor.

12. A process according to claim 11, wherein the backpulse system comprises a first vessel and a second vessel.

13. A process according to claim 12, wherein a backpulse gas from the second vessel increases the pressure in the first vessel, such that the pressure in the first vessel is greater than the reactor pressure.

14. A process according to claim 11, wherein backwards pulses occur periodically, with a period of between about every 5 and 20 minutes.

15. A process according to claim 11, wherein the duration of a backwards pulse is between about 0.2 and 2 seconds.

16. A process according to claim 11, wherein the first reactant is 2-nitro-2-methyl-1-propanol and the second reactant is hydrogen.

17. A process according to claim 13, wherein backwards pulses occur periodically, with a period of between about every 5 and 20 minutes.

18. A process according to claim 13, wherein the duration of a backwards pulse is between about 0.2 and 2 seconds.

19. A process according to claim 15, wherein the first reactant is 2-nitro-2-methyl-1-propanol and the second reactant is hydrogen.

20. A process comprising:
    reacting a nitroalcohol with hydrogen over an activated sponge metal catalyst in a reactor at a reaction pressure between about $2\times10^6$ Pa and about $7\times10^6$ Pa to produce an aminoalcohol, wherein the reactor is a stirred tank slurry reactor;
    filtering the aminoalcohol and the catalyst through a filtration apparatus, such that the catalyst accumulates in the filtration apparatus, wherein the filtration apparatus is located outside of the reactor; and
    returning accumulated catalyst from the filtration apparatus to the reactor using at least one backwards pulse from a backpulse system,
    wherein:
        the backpulse system comprises at least a first vessel and a second vessel,
        a backpulse gas from the second vessel increases the pressure in the first vessel, such that the pressure in the first vessel is greater than the reactor pressure, and
        the backpulse system is provided by a hydraulic piston or a pump and pushes a liquid through the filtration apparatus to return the catalyst accumulated in the filtration apparatus to the reactor.

* * * * *